US008506084B2

(12) United States Patent
Esser et al.

(10) Patent No.: US 8,506,084 B2
(45) Date of Patent: Aug. 13, 2013

(54) METHOD FOR CHECKING AND/OR DETERMINING USER DATA, A COMPUTER PROGRAM PRODUCT, AND AN APPARATUS

(75) Inventors: Gregor Esser, Munich (DE); Anne Seidemann, Munich (DE); Wolfgang Becken, Munich (DE); Edda Wehner, Emmering (DE); Helmut Altheimer, Baisweil-Lauchdorf (DE); Werner Mueller, Oetisheim (DE); Dietmar Uttenweiler, Icking (DE)

(73) Assignee: Rodenstock GmbH, Munich (DE)

( * ) Notice: Subject to any disclaimer, the term of this patent is extended or adjusted under 35 U.S.C. 154(b) by 325 days.

(21) Appl. No.: 12/668,711

(22) PCT Filed: Jul. 14, 2008

(86) PCT No.: PCT/EP2008/005733
§ 371 (c)(1),
(2), (4) Date: Jan. 12, 2010

(87) PCT Pub. No.: WO2009/007136
PCT Pub. Date: Jan. 15, 2009

(65) Prior Publication Data
US 2010/0198817 A1    Aug. 5, 2010

(30) Foreign Application Priority Data
Jul. 12, 2007  (DE) .......................... 10 2007 032 564

(51) Int. Cl.
*A61B 3/00*    (2006.01)
*A61B 3/02*    (2006.01)
*A61B 3/10*    (2006.01)

(52) U.S. Cl.
USPC ........................... 351/246; 351/205; 351/222

(58) Field of Classification Search
USPC ......................................... 351/246, 205, 222
See application file for complete search history.

(56) References Cited

U.S. PATENT DOCUMENTS

| 4,105,302 A | * | 8/1978 | Tate, Jr. .......................... 351/210 |
| 5,796,463 A |   | 8/1998 | Bullimore |

(Continued)

FOREIGN PATENT DOCUMENTS

| DE | 103 48 854 A1 | 5/2005 |
| JP | 04-073038 | 3/1992 |
| JP | 10-028675 | 2/1998 |
| JP | 2002-508674 A | 3/2002 |
| JP | 2004-510525 A | 4/2004 |
| JP | 2005-211423 | 8/2005 |
| JP | 2007-531559 A | 11/2007 |
| WO | WO 2005/058136 A2 | 6/2005 |

OTHER PUBLICATIONS

Max Born et al., Principles of Optics: Electromagnetic Theory of Propagation, Interference and Diffraction of Light, 1980, pp. 203-207; and 459-464, Sixth (Corrected) Edition, Pergamon Press (Thirteen (13) pages).

(Continued)

*Primary Examiner* — Jordan Schwartz
(74) *Attorney, Agent, or Firm* — Crowell & Moring LLP (57) ABSTRACT

The present invention relates in summary to a method for checking and/or determining user data of a spectacle lens user comprising providing subjective data of a spectacle lens user, wherein the subjective data comprise at least subjective refraction data, providing objective refraction data of the spectacle lens user, comparing at least one subset of the subjective refraction data with at least one subset of the objective refraction data and determining a comparison result, matching at least the subset of the subjective refraction data to the objective refraction data on the basis of the comparison result under the assumption that the comparison result fulfills at least one predetermined comparison condition, otherwise maintaining at least the subset of the subjective refraction data and/or providing a message containing the comparison result, and to a further method, a computer program product and two devices for checking and/or determining user data.

15 Claims, 1 Drawing Sheet

(56) References Cited

U.S. PATENT DOCUMENTS

| | | | |
|---|---|---|---|
| 2002/0140902 A1 | 10/2002 | Guirao et al. | |
| 2003/0108350 A1* | 6/2003 | Brauning | 396/661 |
| 2005/0225721 A1 | 10/2005 | Harris et al. | |
| 2005/0264760 A1* | 12/2005 | Ikezawa | 351/239 |
| 2011/0255053 A1 | 10/2011 | Dreher et al. | |
| 2012/0069297 A1* | 3/2012 | Cabeza et al. | 351/205 |

OTHER PUBLICATIONS

Joseph W. Goodman, "Chapter 6: Frequency Analysis of Optical Imaging Systems", Introduction to Fourier Optics, 1968, pp. 101-121.

George Smith et al., The Eye and Visual Optical Instruments, 1997, pp. 97-101; 541-547, and 653-662, 689-690, and 799, 1997, Cambridge University Press, USA.

Larry N. Thibos, Ph.D. et al., "Power Vectors: An Application of Fourier Analysis to the Description and Statistical Analysis of Refractive Error", Optometry and Vision Science, 1997, pp. 367-375, vol. 74, No. 6, XP008078911.

International Search Report dated Dec. 12, 2008 with partial English translation, including Form PCT/ISA/210 and Form PCT/ISA/237 (Seventeen (17) pages).

Japanese Office Action (w/ English Translation), dated Nov. 2, 2012 (Eight (8) pages).

English Translation of Jp 10-028675 of relevant subject matter, Feb. 3, 1998.

English Translation of Jp 04-073038 of relevant subject matter, Mar. 9, 1992.

* cited by examiner

METHOD FOR CHECKING AND/OR DETERMINING USER DATA, A COMPUTER PROGRAM PRODUCT, AND AN APPARATUS

FIELD OF THE INVENTION

The present invention relates to a method for checking and/or determining user data of a spectacle lens wearer, a computer program product, and apparatuses for checking and/or determining user data of the spectacle lens wearer.

BACKGROUND AND SUMMARY OF THE INVENTION

A common method for determining a refraction is the so-called subjective refraction determination, which is widely accepted by opticians. Conventionally, in the subjective refraction determination, the user of a spectacle lens is being presented different spectacle lenses, i.e. spectacle lenses with different optical properties, wherein the user of the spectacle lens informs the refractionist of an improvement or deterioration of the visual impression upon a change of the optical properties of the presented spectacle lens. The subjective refraction determination may e.g. be based on values of an objective refraction determination or on values of already worn spectacles. However, the accuracy of the subjective refraction determination critically depends on the skill of the refractionist, for example an optician and/or ophthalmologist, who performs the subjective refraction determination. Likewise, the subjective refraction determination also critically depends on the person to be examined, in particular on the ability of the person to be examined to assess and/or express the sharpness of the visual impressions.

Often, measuring methods for determining the subjective refraction differ strongly depending on the college of ophthalmic optics, and are also different on an international level. Thereby, greater differences in the results occur.

Furthermore, since the individual refraction lenses are only available in steps of maximally approx. 0.125 D, usually only approx. 0.25 D, the maximum (theoretical) accuracy is usually also only 0.125 D.

In addition, the subjective refraction is only performed with one contrast strength, usually with the maximum contrast and the lowest resolution. It is not checked whether the determined refraction values also represent the ideal refraction values in the case of a bad contrast and a low resolution.

The refraction determination is only performed with one pupillary size, usually with a strong illumination and a small pupil. It is not checked whether the refraction varies along with the pupillary size.

Moreover, the ambient parameters may sometimes vary very strongly depending on the examination location, and have a significant, uncontrollable influence on the result. The ambient parameters are e.g. contrast of the eye test, distance of the eye test, size of the optotypes, shape of the optotypes, and room brightness. Therefore, the subjective refraction often only provides results far from satisfactory.

It is therefore an object of the present invention to provide refraction data of a user of a spectacle lens in a simple manner.

This object is achieved by the method, by the computer program product, and by the apparatus of the independent claims. Preferred embodiments are subject of the dependent claims.

Method According to One Aspect of the Invention

One aspect of the present invention relates to a method for checking and/or determining user data of a spectacle lens user, comprising the steps of:

providing subjective data of a spectacle lens user, wherein the subjective data at least comprise subjective refraction data;

providing objective refraction data of the spectacle lens user;

comparing at least a subset of the subjective refraction data with at least a subset of the objective refraction data, and determining a comparative result;

matching at least the subset of the subjective refraction data to the objective refraction data on the basis of the comparative result provided that the comparative result fulfils at least one predetermined comparative condition, otherwise, maintaining at least the subset of the subjective refraction data and/or providing a message containing the comparative result.

Advantageously, the subjective refraction measurement and the objective refraction measurement are combined with each other. For example, deviations between the subjective and the objective refraction may occur due to adaptations of the visual system. These deviations can be easily and safely be determined and be compensated for if need be. In particular, it may advantageously be checked whether the determined refraction values are physiologically compatible with the future users. For example, it often happens that the "perfect" imaging, i.e. an imaging according to objective refraction data, is subjectively not considered to be the best, since the visual system has already adapted to the faulty refraction in sensoric terms. For example, if the user has a slight hyperopia, the user can compensate for this hyperopia by means of accommodation as long as he/she is not presbyopic. If e.g. such a hyperopia is fully corrected on the basis of the objective refraction data, this may lead to incompatibility. The same applies to astigmatic visual defects. In this case, however, the difference between subjective and objective refraction data may be even more significant. For example, a full correction on the basis of objective refraction data may subjectively not be considered to be the best correction. However, according to the present invention, it is possible to determine e.g. (significant) deviations of the subjective refraction data from the objective refraction data and to thereby find out whether the refractionist has performed a faulty refraction determination. If need be, the subjective refraction data can be matched to the objective refraction data at least partially. Additionally or alternatively, the values obtained by the subjective refraction measurement can be maintained for at least a part of the refraction data even if these values deviate from the objective refraction data. In particular, a comparative condition can be set, wherein no adaptation of the subjective refraction data is made if the difference between the objective refraction data and the subjective refraction data is less than the comparative condition. As an example, a maximum deviation of the spherical refractive power, the astigmatism, in particular the axial position of the astigmatism, etc., may be set or predetermined and, as long as the deviation is smaller than the maximum predetermined deviation, no adaptation of the subjective refraction data is made. As a further example, a maximum value of the sphere and/or the cylinder of the deviation, calculated according to the cross-cylinder method, between the subjective and the objective refraction data may be set. In both cases, the maximally admissible deviation may be 0.1 D, 0.2 D, 0.5 D, 1 D, 2 D, etc. In other words, the comparative condition may correspond to the maximally admissible deviation. The maximum deviation may as well be a relative value, for example one percent. The maximum deviation, i.e. the comparative condition, may be a difference between an objective and a subjective value (or several such values) between approx. 1% and approx. 50%, in particular between approx. 10% and approx. 30%, e.g. also a deviation of approx. 1%, 2%, 3%, 5%, 10%, 15%, 20%, 25%, etc.

Alternatively or in addition, a message containing the comparative result may be output. In particular, the message may be a warning message, which indicates that e.g. a subset of the subjective refraction data and a subset of the objective refraction data do not meet a predetermined comparative condition, i.e. that a deviation of at least a subset of the subjective refraction data from the corresponding objective refraction data is present which is e.g. greater than a predetermined comparative condition. In a next step, the refractionist may e.g. manually change the subjective refraction data, in particular match them to the objective refraction data. The refractionist may as well repeat the subjective refraction determination at least partially. It is also possible to automatically match the subjective refraction data to the objective refraction data.

The term "providing" as defined by the present invention includes "measuring", "estimating", "transferring", "taking from a database and/or a table", "sending", etc.

The subjective data include at least subjective refraction data. The subjective data may also include further data, such as the age of the spectacle lens user, a development of the visual defect of the spectacle lens user, a medical history of the spectacle lens user, etc.

The subjective data may be collected e.g. by an optician, an ophthalmologist, etc. The subjective data may also be available from a local database or one incorporated in a network, or from a server-based database, or an external database, etc. This data may be completed with the subjective refraction data or the subjective refraction data may be renewed after refraction determination. For example, the subjective data may be transferred to a spectacle lens manufacturer. This transfer may be by mail, for example. The subjective data may as well be transferred via a network, for example the Internet, etc.

Also, the objective refraction data may be taken from a database and be updated by the optician, the ophthalmologist, etc. The objective refraction data may (subsequently) be transferred to a spectacle lens manufacturer.

The objective refraction data and/or at least a subset of the subjective data may also be deposited with the spectacle lens manufacturer.

Moreover, the comparison of at least the subset of the subjective refraction data with at least the subset of the objective refraction data may be performed at the optician, ophthalmologist, etc., and likewise, comparative results may be output there and at least a subset of the subjective refraction data be adapted if need be. Alternatively or in addition, the comparison, optionally the adaptation and/or the outputting of the message may also take place at the spectacle lens manufacturer.

Matching at least the subset of the subjective refraction data to the objective refraction data may in particular include changing one or more values of the subjective refraction data. For example, a value of the subjective refraction data, which deviates from a value measured by means of objective refraction, may be matched to the value determined by objective measurement. The value of the subjective refraction measurement may e.g. be equated with the value of the objective refraction measurement. The value of the subjective refraction measurement may as well be equated with the average value of the subjective and the objective refraction value. It is also possible for the subjective refraction value to be increased or decreased by 5%, 10% or 15%, 20%, etc., of the difference of the value of the subjective refraction measurement and the objective refraction measurement.

By means of the combination of the subjective refraction data and the objective refraction data, in particular by means of the possible selective change of subjective refraction data and/or by maintaining the subjective refraction data, also if they deviate from the objective refraction data, an intended deviation of the subjective refraction data from the objective refraction data in particular due to geometrical-optical imaging differences may advantageously be maintained. Such imaging differences may occur due to the distance spectacle lens-eye in particular in a correction of astigmatic visual defects, since a strange distortion may be present owing to the distance spectacle lens-eye. Since also in this case a full correction according to objective refraction data is often subjectively not considered to be the best correction, it may be advantageous to not match the subjective refraction data or only a subset of the subjective refraction data to the objective refraction data. It is also possible to only match the subjective refraction data to the objective refraction data e.g. by a few percentage points (1%, 2%, 3%, 5%, 10%, etc.). Thus, the influence of geometrical-optical imaging differences can advantageously be taken into account.

Further preferably, by means of the combination of subjective and objective refraction measurements, binocular vision can be taken into account, which is particularly neglected in conventional objective measuring methods. Here, binocular vision has a great influence on the refraction values due to the strong coupling of accommodation and convergence. In the case of exophoria, a divergence excess and/or a convergence insufficiency, often great differences between the monocular and binocular refraction values occur. For example, binocular values shift toward minus, since with the therefor required accommodation and the resulting convergence, the exophoria, i.e. a two-part, outward deviation of the visual axis, is compensated for. Conversely, in the case of esophoria, a divergence insufficiency or convergence excess, i.e. inward strabismus, the values often shift toward plus. In a subjective refraction determination, these influences can be taken into account, since in particular the subjective refraction determination is possible in a binocular manner. By correspondingly adapting the comparative conditions, the subjective refraction data and the objective refraction data can be compared with each other, and for example a deviation of the subjective refraction data from the objective refraction data may be allowed due to the binocular subjective refraction measurement.

Further advantageously, in particular due to a schematic approach in a subjective refraction determination, accommodation may be controlled or taken into account. It is often difficult to determine the influence of accommodation on an objective refraction measurement, or it cannot be taken into account.

Preferred Variants of the Method

According to a preferred variant, target values of at least one spectacle lens are determined on the basis of the following data:
  at least a subset of the subjective refraction data and/or
  at least a subset of the adapted subjective refraction data and/or
  at least a subset of the objective refraction data.

The term "determining" as defined by the present application includes calculating or estimating at least one target value. For example, on the basis of the predetermined data, a target value may be taken from a database and/or be calculated by means of predetermined optimisation algorithms. Here, one or more optimisation methods may be used.

The term "target value" as defined by the present application includes a desired value of a spectacle lens. In other words, the target value of the spectacle lens is the value corresponding to the defaults set by an optician, an ophthalmologist and/or a manufacturer. The target value may comprise several values. The target value may in particular include values for the spherical power, cylinder, axis, etc., which the spectacle lens is to have. In an ideal spectacle lens, the actual optical properties correspond to the target value.

Further preferably, the subjective refraction data and/or the matched subjective refraction data and/or the objective refraction data are combined to form combined refraction data.

Here, the subjective refraction data may be the refraction data provided by subjective refraction measurement. The matched subjective refraction data may e.g. be the subjective refraction data matched on the basis of the objective refraction data, or a subset of these subjective refraction data. The objective refraction data are the objective refraction data provided by means of an objective method.

In particular, a subset or a total of the aforementioned data may be used. For example, target values may be determined on the basis of combined objective refraction data formed by combination of
  at least a subset of the subjective refraction data and/or
  at least a subset of the matched subjective refraction data and/or
  at least a subset of the objective refraction data.

Further preferably, effective objective refraction data are generated on the basis of at least a subset of the objective refraction data, wherein for determining the comparative results, the effective objective refraction data are compared with at least a subset of the subjective refraction data. For example, a variety of objective refraction data may be generated among others for a variety of pupillary sizes, different boundary conditions, such as brightness, contrast, etc., and the effective objective refraction data may be generated or determined on the basis of this variety of objective refraction data. For example, it is possible that merely a part of the objective refraction data is changed to form effective objective refraction data. The rest of the objective refraction data remains unchanged. The total of these effective objective refraction data and of the remaining objective refraction data may be referred to as effective objective refraction data. These effective objective refraction data may be compared with the subjective refraction data.

For example, it is possible to determine target values on the basis of combined objective refraction data formed by combination of
  at least a subset of the subjective refraction data and/or
  at least a subset of the matched subjective refraction data and/or
  at least a subset of the objective refraction data.

According to a further preferred embodiment, several sets of objective refraction data are provided, and the effective objective refraction data are generated on the basis of the several sets of objective refraction data. The sets of objective refraction data may e.g. be generated for different boundary conditions (see above).

For example, the effective objective refraction data are determined taking the following boundary conditions into account:
  brightness and/or
  pupil diameter and/or
  contrast and/or
  age.

Preferably, for calculating the effective objective refraction data, an aberration function or wave function and/or an optical transfer function (referred to as "OTF") and/or a modulation transfer function (referred to as "MTF") and/or a so-called point spread function (referred to as "PSF") and/or a standard deviation and/or a Strehl ratio are calculated. In this connection, reference is made to the relevant literature. Precise definitions of the aberration function are e.g. found in the book "Principles of Optics" by Born and Wolf, Pergamon Press (1980), pages 203 ff. and pages 459 ff. A definition of the Strehl ratio is given on pages 462 ff. Definitions of "OTF" and "MTF" as well as a discussion thereof are given in the book "Introduction to Fourier Optics" by Goodman, McGraw-Hill, 1968. The point spread function ("PSF") is the Fourier transform of the "OTF" and is the point image function, i.e. describes the intensity distribution of the image which an optical systems forms from a point-shaped light source. PSF is e.g. defined and explained in the "The eye and visual optical instruments", by Smith/Atchison, Cambridge University Press, 1996.

Particularly preferably, an aberration function is taken into account, wherein the considered order of the aberration is variable.

In other words, the order of the aberration can be selected once and be maintained then. It is also possible to change the order of the aberration continuously or stepwise or iteratively, etc.

According to a further preferred embodiment, at least a subset of the objective refraction data is determined by means of eccentric photorefraction.

In particular, at least the subset of the objective refraction data may be determined in a monocular or binocular manner.

Method According to a Further Aspect of the Invention

A further aspect of the present invention relates to a method for checking and/or determining user data of a spectacle lens wearer, comprising the steps of:
  providing objective refraction data of the spectacle lens user;
  determining effective objective refraction data, wherein the effective objective refraction data are generated on the basis of at least a subset of the objective refraction data; and
  determining target values of at least one spectacle lens on the basis of the effective objective refraction data.

Further, with respect to this method, the aforementioned preferred variants and the aforementioned advantages analogously apply as well.

Further preferably, at least one of the aforementioned methods comprises the step of:
manufacturing the at least one spectacle lens on the basis of the determined target values.

Computer Program Product According to One Aspect of the Invention

A further aspect of the present invention relates to a computer program product, in particular stored on a computer-readable medium or realized as a signal, which, when loaded into the memory of a computer and executed by a computer, causes the computer to execute an inventive method.

Apparatus According to One Aspect of the Invention

A further aspect of the present invention relates to an apparatus for checking and/or determining user data of a spectacle lens user, comprising:
  a subjective data providing device adapted to provide subjective data of a spectacle lens user, wherein the subjective data comprise at least subjective refraction data;
  an objective data providing device adapted to provide objective refraction data of the spectacle lens user;

a comparing device adapted to compare at least a subset of the subjective refraction data with at least a subset of the objective refraction data, and adapted to determine a comparative result;

a matching device adapted to match at least the subset of the subjective refraction data to the objective refraction data on the basis of the comparative result provided that the comparative result fulfills at least a predetermined comparative condition, wherein the matching device is adapted to otherwise maintain at least the subset of the subjective refraction data and/or wherein the comparing device is adapted to provide a message containing the comparative result.

Apparatus According to a Further Aspect of the Invention

A further aspect of the present invention relates to an apparatus for checking and/or determining user data of a spectacle lens user, comprising:

an objective data providing device adapted to provide objective refraction data of a spectacle lens user;

a determining device adapted to determine effective objective refraction data, wherein the effective objective refraction data are generated on the basis of at least a subset of the objective refraction data;

a determining device adapted to determine target values of at least one spectacle lens on the basis of the effective objective refraction data.

Preferred Embodiments of the Apparatuses

Preferably, one of said apparatuses comprises a manufacturing device adapted to manufacture at least one spectacle lens on the basis of the determined target values.

Further preferably, the aforementioned explanations and advantages with respect to the methods analogously also apply to the aforementioned apparatuses. In particular, the aforementioned apparatuses have means or devices adapted to perform the aforementioned method steps.

BRIEF DESCRIPTION OF THE DRAWINGS

Preferred variants and preferred embodiments of the present invention will be described by way of example in the following on the basis of accompanying figures, which show.

DETAILED DESCRIPTION OF THE PREFERRED EMBODIMENTS

Figure 1:
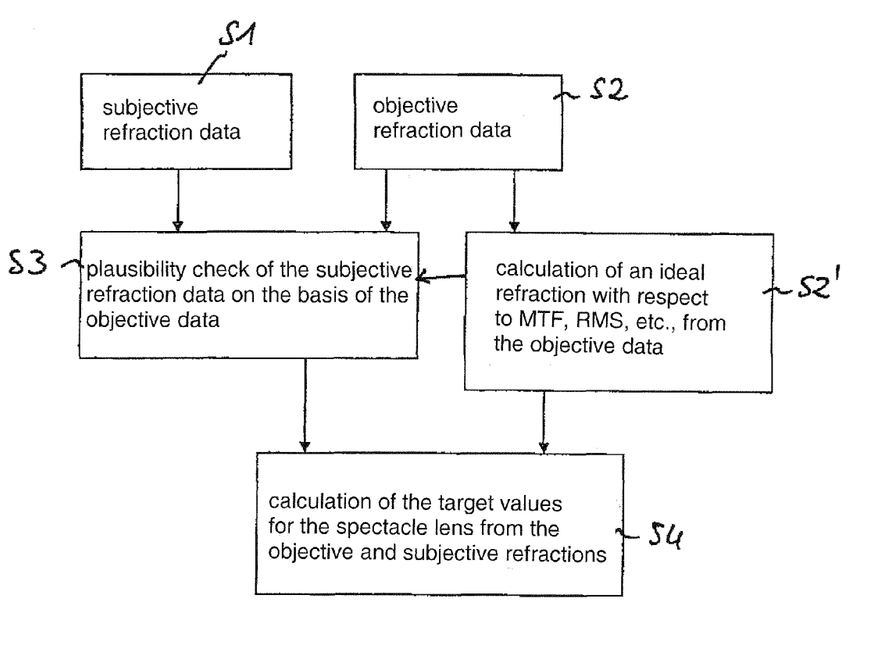
FIG. 1 describes exemplary methods for checking user data of a spectacle lens wearer and for manufacturing a spectacle lens.

In step S1 of FIG. 1, subjective data of the user are determined, i.e. the subjective data are provided. In particular, subjective refraction data are determined in step 1. The subjective data include for example information about the age, the development of the visual defect of the user, the sex of the user, profession of the user, a medical history, etc. The subjective refraction data in particular include one or more conventional refraction data, such as sphere, cylinder, axial position, etc.

The subjective data may also include individual parameters of the user, such as pupillary distance, corneal vertex distance, face form forward inclination, etc. The subjective refraction data may be measured e.g. at an optician's. Likewise, further subjective data may be measured at an optician's or be provided to the optician by the user. Alternatively, this may also take place at the ophthalmologist's. For example, it is also possible for a part of the subjective data to be deposited with the ophthalmologist and a part of the subjective data to be deposited with an optician. The data may be exchanged between the ophthalmologist and the optician. Additionally or alternatively, the data may also be transferred to a spectacle lens manufacturer by the ophthalmologist and/or the optician. The transfer may in particular take place by mail. However, the transfer may also take place via a fax machine, the Internet, by means of a storage medium, etc. For example, the ophthalmologist may provide the spectacle lens manufacturer with a subset of the subjective data by mail. The optician may transfer a part of the subjective data to the manufacturer by e-mail. Optionally, the user of the spectacle lens may provide a part of the subject data to the optician and/or the ophthalmologist; in particular, these data may be stored on a memory chip, in particular a digital/electronic health insurance card, etc.

In a further step S2, objective refraction data are provided. The objective refraction data may e.g. be measured by one or more objective refraction measurements at an ophthalmologist's or an optician's and/or be exchanged between the ophthalmologist and the optician. The objective refraction data may as well be transferred to the spectacle lens manufacturer.

In a step S3, a plausibility check of the subjective refraction data may be performed on the basis of the objective refraction data. In other words, the subjective refraction data and the objective refraction data can be compared with each other, and deviations of the subjective and objective refraction data can be determined. This plausibility check may also be performed e.g. at the ophthalmologist's, the optician's, or also at the manufacturer's. For example, a part of the data may be checked for plausibility at the ophthalmologist's and/or the optician's. A part of the data may also be checked for plausibility at the manufacturer's. It is also possible for the data to be checked for plausibility both at the ophthalmologist's and the optician's and the manufacturer's.

Subsequently, in a further step S4, target values for the spectacle lens may be generated from the objective and the subjective refraction data. In particular, it may e.g. be possible to merely use the subjective refraction data for determining the target values of the spectacle lens after the subjective refraction data have been checked for plausibility on the basis of the objective refraction data. Alternatively, the subjective refraction data and the objective refraction data may be taken into account in the determination of the target values; for example, subjective refraction values or data may be corrected on the basis of the objective refraction data. It is also possible for a subset of the subjective refraction data and a subset of the objective refraction data to be taken into account in order to calculate, in particular determine target values of the spectacle lens and optimise a corresponding spectacle lens. The target values may be determined at the ophthalmologist's and/or the optician's and/or the manufacturer's on the basis of the subjective refraction values and/or the objective refraction values. If the target values are not determined at the manufacturer's, the target values are provided to the manufacturer in a further step. It is also possible for the manufacturer to obtain the subjective and/or objective refraction values in addition to the target values, and thus the target values may be checked by the manufacturer as well or the manufacturer may determine his own target values.

Further preferably, in a step S2', an ideal refraction with respect to MTF and/or RMS, etc. may be determined, in particular calculated, from the objective refraction data. The ideal refraction data may as well be referred to as effective objective refraction data. Subsequently, it is possible to perform in the aforementioned step S3 the plausibility check of the subjective refraction data on the basis of the effective objective refraction data as calculated in step S2'.

Alternatively, after calculation of the effective objective refraction data, it is also possible to determine target values on the basis of the effective objective refraction data in step S4. Here, it is not necessary to take the subjective refraction values into account. It is also possible to take into account the subjective refraction values and/or the effective objective refraction values in step S4.

Furthermore, in step S4, the further subjective data of the user may be taken into account in the determination or calculation of the target value.

In other words, by means of combined refraction values determined on the basis of the subjective refraction values, and/or the further subjective data and/or the objective refraction data, in particular the effective objective refraction data, a spectacle lens or both spectacle lenses of the user are determined. The determination may comprises a calculation and/or an optimisation and/or a loading of data from a database.

Consequently, on the one hand, the subjective refraction determination may exhibit a number of deficiencies and it may particularly be possible to determine, in particular calculate and optimise spectacle lenses with increasing precision. On the other hand, in order to use the technical possibilities to the fullest, it is necessary to provide refraction values representing the target values for the spectacle lens, wherein the refraction values have to be determined as exactly as possible, since otherwise e.g. advantages of an individual optimisation in a position of wear are substantially neutralised. According to the invention, it has been found out to compensate for the disadvantages and deficiencies of a subjective refraction determination by means of the more and more precise objective measuring methods, wherein by means of better and better measuring methods, a substantially complete aberration function can be described and evaluated for example with the help of aberrometers. It is possible to therefrom calculate an ideal refraction e.g. for different pupil diameters or for different contrasts. Here, advantageously, the Stiles-Crawford effect, the weighting of the pupil, etc., can be taken into account. Furthermore, it may be possible to calculate the best target values for the spectacle lens to be determined in view of different brightness levels and pupillary sizes, different weighting functions of the pupil, different contrasts, for optimum values or distributions of RMS, PSF, OTF, MTF and/or the Streh ratio. Likewise, other measures may be considered in the assessment of vision quality, such as entropia of the PSF, visus of the visual system NS, and a number of further conventional methods.

According to the invention, it has been advantageously found out to combine the advantages of a subjective refraction determination as described above, which an objective refraction determination can regularly not provide, with the precision of an objective refraction determination. Here, no longer only the values of the subjective refraction determination are provided e.g. by an optician or an optometrist or an ophthalmologist, but also values of an objective measurement. The values of the subjective and/or the objective measurement may be transferred to a manufacturer and/or be exchanged between the optician, the optometrist and/or the ophthalmologist.

The objective measurement may be performed e.g. by means of a skiascope, by means of eccentric photorefraction, by means of an auto refractometer and/or an aberrometer. The objective measurement may also comprise eccentric photorefractions. Preferably, a measurement with a large pupillary opening is included. Further preferably, the measurement is performed with an aberrometer, since thereby substantially the entire aberration function becomes known and the above optimisation can be performed, in particular calculated, very easily therefrom.

Further preferably, as mentioned above, a plausibility check of the subjective refraction data may be performed. For example, in the subjective refraction determination, an axis of a cylinder may be twisted by approx. 90°. This can easily be checked by means of the objective refraction data and be corrected if need be. Furthermore, it may e.g. be checked whether the differences between the subjective refraction measurement and the objective refraction measurement are plausible. A slightly weaker cylinder in the subjective refraction measurement can be considered to be acceptable and thus does not have to be corrected. In particular, conventionally, a cylinder determined by subjective refraction measurement is often weaker than a cylinder determined by objective refraction measurement. Moreover, no correction has necessarily to be made that the spherical values, as determined by the subjective refraction measurement, deviate approximately to an equal extent toward plus or minus with respect to the objective values on both sides (i.e. for the left and the right eye). Optionally, as mentioned above, corrections may be made in order to thus improve the target values for the spectacle lens for example by means of a suitable algorithm. The correction may be made manually or automatically.

Particularly advantageously, by means of the combination of the subjective and objective refraction data, as shown in step S4, improved target values for a spectacle lens can be determined, in particular calculated, as this is in comparison therewith not possible only by means of the individual subjective refraction measurement or the individual objective refraction measurement. For example, it is possible to find a better correction for different ambient parameters, which comprise e.g. brightness, contrast, etc., from the objective measurement, in particular the eccentric photorefraction or aberrometer measurement, than this is conventionally possible.

Preferably, in a possible correction algorithm, it is taken into account whether a change can be compensated for by accommodation. If e.g. the refraction values tend more toward minus when the pupil is large, it may optionally be derived therefrom that an averaging of the values between small and large pupil leads to an improvement in large pupils, while in small pupils no deterioration occurs due to the compensation by the accommodation and an increased focal depth. In the case of a shift toward plus, however, this may be more critical.

Further preferably, it is avoided that due to a change of the correction strength as a result of the objective measuring results, for example when the pupil is large, the progressive myopia is fostered in addition. In doing so, variables may be detected which may also be used to assess how stable or progressive the individual myopia is. Such variables may be age, phoria, myopia progression per year, time passed since the beginning of myopia development, etc., which are taken into account in the subjective data. Preferably, these variables are taken into account in order to avoid the myopia progression from accidentally being increased with the new calculated, optionally stronger minus correction. Advantageously, not only the best-possible imaging with differently large pupils is achieved, but also a correction can be achieved which, if necessary, does not foster the myopia progression more strongly than the usual correction or further advantageously inhibits the myopia progression.

In addition to spherical and/or cylindrical refraction values, also aberrations, in particular of higher order, as well as the subjective refraction may be taken into account. In the evaluation of this measurement, different measured pupillary sizes may be taken into account, as well as the average pupillary size and optionally their variance typical of the user's age group.

Moreover, by means of simulation of different aberrations and/or individual or combined aberration terms, the compatibility and the benefit of possible corrections can be determined. This has to take place both spontaneously and after some time of adaptation. In doing so, it may be taken into account that not every aberration has to be corrected fully to allow for a high visus and/or a high visual quality. Furthermore, it may be taken into account that in particular the effects of higher-order aberrations are strongly influenced by the variance of the pupillary size. In addition, the focal depth, which influences all aberrations, may be taken into account in the decision as to which aberration is to be corrected how strongly.

Further preferably, the correction does not have to be performed only according to measurement values, but also by weighting of individual, physiologically-justified, further and/or different factors. Consequently, for correction it is possible to calculate different terms together in order to be able to correct some or several aberrations in the form of few or some terms in the spectacle lens in the best possible way. Alternatively or in addition, the subjective refraction can be determined with different pupillary sizes. Possible differences of the subjective refraction values at different pupillary sizes may be optionally or additionally be taken into account in the optimisation of the correction values. Further preferably, for calculation of the prescription values and/or target values of a spectacle lens from the subjective and objective refraction determination, the objective refraction determination is performed with eccentric photorefraction, wherein a selection is made as to whether the measurement is to be performed in a monocular or binocular manner. Here, the number and the order of the aberrations taken into account may be variable.

In the following, a preferred variant of the combination of the subjective and objective data of the refraction determination will be described, which allows for the determination, in particular calculation, of an improved description or improved target values for a spectacle lens.

Mathematical Representation of a Combination of Objective Refraction and Subjective Refraction Parameters of objective refraction:
spherical power: sph_obj
cylindrical power: zyl_obj
axial position: A_obj
Parameters of subjective refraction:
spherical power: sph_sub
cylindrical power: zyl_sub
axial position: A_sub
Power vector:
As a power vector there is defined:

$$P = \begin{pmatrix} M \\ J_0 \\ J_{45} \end{pmatrix}, \quad (1)$$

where P is merely short for a variety of possible power vectors for a variety of possible data sets. For example, a power vector $P_{obj,r}$ may include values of objective refraction for the right eye, i.e. in particular $M_{r,obj}$, $J_{0,r,obj}$ and $J_{45,r,obj}$, a power vector $P_{obj,l}$ may include values of objective refraction for the left eye, i.e. in particular $M_{l,obj}$, $J_{0,l,obj}$ and $J_{45,l,obj}$, a power vector $P_{sub,r}$ may include values of subjective refraction for the right eye, i.e. in particular $M_{r,sub}$, $J_{0,r,sub}$ and $J_{45,r,sub}$, a power vector $P_{sub,l}$ may include values of subjective refraction for the left eye, i.e. in particular $M_{l,sub}$, $J_{0,l,sub}$ and $J_{45,l,sub}$. Furthermore, it is possible to take into account different pupil diameters in the data sets of the objective refraction data, in which the objective refraction data were generated, in particular calculated. Consequently, i power vectors $P_{obj,r}^i$ and/or $P_{obj,l}^i$ may be present, which include objective refraction values for i different pupil diameters $DP_r^i$ of the right eye or for different pupil diameters $DP_l^i$ of the left eye, where i is a natural number.

Analogous explanations also apply to further variables or parameters, as far as applicable.

The vector components of the power vector will be defined in the following:

$$M = sph + \frac{zyl}{2} \quad (2)$$

$$J_0 = -\frac{zyl}{2}\cos 2A,$$

$$J_{45} = -\frac{zyl}{2}\sin 2A$$

where the vector components are indicated in short—as above—for the sake of clarity. With respect to the objective refraction data of the left eye for a pupil diameter $DP_l^i$, the spherical equivalent is e.g. referred to as $M_{l,obj}$.

The above representation may be reformulated as follows:

$$zyl = -2\sqrt{J_0^2 + J_{45}^2} \quad (3)$$

$$sph = M - \frac{zyl}{2}$$

$$A = \frac{1}{2}\arctan\frac{J_{45}}{J_0}$$

$$A = \begin{cases} 45°; & J_0 = 0 \wedge J_{45} \leq 0 \\ 135°; & J_0 = 0 \wedge J_{45} > 0 \\ \frac{1}{2}\arctan\frac{J_{45}}{J_0}; & J_0 < 0 \wedge J_{45} \leq 0 \\ \frac{1}{2}\arctan\frac{J_{45}}{J_0} + 180°; & J_0 < 0 \wedge J_{45} > 0 \\ \frac{1}{2}\arctan\frac{J_{45}}{J_0} + 90°; & J_0 > 0 \end{cases} \quad (4)$$

1. Plausibility Check of the Subjective Refraction Data on the Basis of the Objective Refraction Data Calculation of the difference vector $P_{Dif}$ between the objective and subjective refraction data for the right and left eyes each:

$$P_{Dif,r} = \text{abs}(P_{obj,r} - P_{sub,r})$$

$$P_{Dif,l} = \text{abs}(P_{obj,l} - P_{sub,l}). \quad (5)$$

If the maximum value of the individual vector components of the vectors $P_{Dif,r}$ and $P_{Dif,l}$ exceeds a specified bound S, a refractionist (e.g. optician, ophthalmologist, optometrist) may be informed and/or a check of the subjective refraction may be initiated.

In other words, if it holds that:

$$\text{Max}(P_{Dif,r}(1), P_{Dif,r}(2), P_{Dif,r}(3), P_{Dif,l}(1), P_{Dif,l}(2), P_{Dif,l}(3)) \geq S \quad (6)$$

preferably a refraction is informed and/or the subjective refraction data are checked.

Further preferably, it holds that:

$$S \leq 1.00 \text{ dpt.} \quad (7)$$

Alternatively or in addition, when the norm of the difference of the power vectors $P_{Dif,r}$ and $P_{Dif,l}$ of a specified bound S is exceeded, the refractionist (e.g. optician, ophthalmologist, optometrist) may be informed and/or a check of the subjective refraction may be initiated.

2. Simulation of Binocular Matching a. Calculation of the binocular difference between the right and left eyes $$M_{Dif} = M_r - M_l, \quad (8)$$

where $M_{Dif}$ is short for $M_{Dif,obj}$ or $M_{Dif,sub}$ and $M_r$ is short for $M_{r,obj}$ or $M_{r,sub}$ and $M_l$ is short for $M_{l,obj}$ or $M_{l,sub}$.

b. Calculation of the difference between the subjective and objective differences $$\text{Dif} = M_{Dif,obj} - (g_{obj\_bino} M_{Dif,obj} + g_{sub\_bino} M_{Dif,subj})$$

$$g_{obj\_bino} = 1 - g_{sub\_bino}$$

$$0 < g_{sub\_bino} < 1 \quad (9)$$

Preferably, it holds that:

$$g_{sub\_bino} \geq 0.6 \quad (10)$$

Particularly preferably, it holds that:

$$g_{sub\_bino} = 0.9 \quad (11)$$

c. Matching of the objective data

It holds that:

$$M^*_{r,obj} := M_{r,obj} - \frac{\text{Dif}}{2} \quad (12)$$

$$M^*_{l,obj} := M_{l,obj} + \frac{\text{Dif}}{2}.$$

For the sake of clarity, $M^*_{r,obj}$ is again referred to as $M_{r,obj}$ in the following formalism. Likewise, $M^*_{l,obj}$ is again referred to as $M_{l,obj}$ in the following formalism.

Therefrom, the spherical power on the left and right can be calculated with $$sph = M - \frac{zyl}{2} \quad (13)$$

wherein preferably cylinder and axial position remain unchanged. As explained above, the spherical power $sph_r$ can be determined for the right eye and the spherical power $sph_l$ for the left eye. In particular, the spherical power may be defined as follows:

$$sph_r = M_{r,obj} - \frac{zyl_r}{2} \quad (14)$$

and/or $$sph_l = M_{l,obj} - \frac{zyl_l}{2}. \quad (15)$$

It is also possible that the following combination of the subjective and objective refractions is performed without binocular matching.

3. Combination of the Subjective and Objective Refractions

The resulting new refraction $P_K$ is calculated from the subjective and objective refractions as follows:

$$P_K = G_{obj} P_{obj} + G_{sub} P_{sub} \quad (16)$$

where it holds that:

$$G = \begin{pmatrix} g_1 & 0 & 0 \\ 0 & g_2 & 0 \\ 0 & 0 & g_3 \end{pmatrix}, \quad (17)$$

$$0 < g_i < 1, \quad (18)$$

and $$G_{obj} + G_{sub} = 1. \quad (19)$$

Preferably, it holds that:

$$g_{sub,i} \geq 0.5. \quad (20)$$

Particularly preferably, it holds that:

$$g_{sub,1} \geq 0.6 \ \ g_{sub,2} \geq 0.5 \ \ g_{sub,3} \geq 0.7 \ \text{and} \ \text{Abs}(g_{sub,2} - g_{sub,3}) \leq 0.3. \quad (21)$$

Most preferably, it holds that:

$$g_{sub,1} \geq 0.7 \ \ g_{sub,2} \geq 0.6 \ \ g_{sub,3} \geq 0.8 \ \text{and} \ \text{Abs}(g_{sub,2} - g_{sub,3}) \leq 0.1. \quad (22)$$

4. Determination of Addition

Addition Add $$Add_r = Add - M_{K,r} + M_{sub,r} \quad (23)$$

$$Add_l = Add - M_{K,l} + M_{sub,l}.$$

$$Add_K = \frac{Add_r + Add_l}{2}$$

Advantageously, a shift in the distance is compensated for.

In order to not change the near value determined in the subjective refraction determination, the addition has to be correspondingly adapted by the amount the spherical equivalent M is changed in the distance, since the addition represents the difference between distance and near values.

5. Determination of Spectacles when Binocular Problems Exist

If further information on the binocular status exist, the determination of the spherical equivalent M and the addition Add may also take place in a different way by means of a different and/or additional approach with respect to item 3 as described above:

a. Convergence Insufficiency

Features: low ACA gradient, no accommodation deficiency in the near, exophoria, i.e. a horizontal phoria in which the fusion simulation-free rest position deviates outward from the ortho position, in the near, low maximum convergence, bad positive and good negative relative vergence in the near, bad negative and good positive relative accommodation in the near. The term ACA gradient describes the accommodative vergence that is coupled with a change of the accommodation condition by one diopter. The abbreviation ACA stands for the English term accommodative vergence divided by accommodation.

Different from the approach described above in item 3, the spherical equivalent $M_K$ of the combination and the addition may be determined as follows:

$$g_{subj,2} \geq 0.6 \; g_{subj,3} \geq 0.8 \quad (24)$$

$$M_K = \min\left(\frac{M_{obj} + M_{sub}}{2}, M_{sub}\right) \quad (25)$$

$$Add_r = Add - \max(0, M_{K,r} - M_{sub,r})$$

$$Add_l = Add - \max(0, M_{K,l} - M_{sub,l})$$

$$Add_K = \min(Add_r, Add_l) \quad (26)$$

b. Convergence Excess

Features:

high ACA gradient, accommodation deficiency in the near, esophoria, i.e. a horizontal phoria in which the fusion simulation-free rest position deviates inward from the ortho position, in the near, great maximum convergence, good positive and bad negative relative vergence in the near, good negative and bad positive relative accommodation in the near.

Different from the approach described above in item 3, the spherical equivalent $M_K$ of the combination may be determined as follows:

$$g_{subj,2} \geq 0.6 \; g_{sub,3} \geq 0.8 \quad (27)$$

$$M_K = \max\left(\frac{M_{obj} + M_{sub}}{2}, M_{sub}\right) \quad (28)$$

$$Add_r = Add - \min(0, M_{K,r} - M_{sub,r})$$

$$Add_l = Add - \min(0, M_{K,l} - M_{sub,l})$$

$$Add_K = \max(Add_r, Add_l) \quad (29)$$

c. Exophoria

Features:

exophoria in the distance and near, normal ACA gradient, low maximum convergence, bad positive and good negative relative vergence, bad negative and good positive relative accommodation.

Different from the approach described above in item 3, the spherical equivalent $M_K$ of the combination may be determined as follows:

$$M_K = \min(M_{obj}, M_{sub}) \quad (30)$$

$$g_{subj,2} \geq 0.6 \; g_{subj,3} \geq 0.8. \quad (31)$$

d. Esophoria

Features:

esophoria in the distance and near, normal ACA gradient, great maximum convergence, good positive and bad negative relative vergence, good negative and bad positive relative accommodation.

Different from the approach described above in item 3, the spherical equivalent $M_K$ of the combination may be determined as follows:

$$M_K = \max(M_{obj}, M_{sub}) \quad (32)$$

$$g_{subj,2} \geq 0.6 \; g_{subj,3} \geq 0.8. \quad (33)$$

6. Determination of Spectacles for Twilight Vision (Mesopic Vision)

Additionally or alternatively to the method described above in items 2 and 3, the following may take place for the right and left eyes each:

a. Calculating the objective refraction data from the wavefront data of the aberrometer measurement for photopic vision:

$$P_{obj,ph}. \quad (34)$$

b. Calculating the objective refraction data from the wavefront data of the aberrometer measurement for a large pupil diameter for mesopic vision:

$$P_{obj,sk}. \quad (35)$$

c. Calculating the difference between the photopic and the mesopic objective refraction:

$$P_{Dif} = P_{obj,sk} - P_{obj,ph}. \quad (36)$$

d. Calculating a subjective refraction for mesopic vision from the normal subjective refraction and the difference between the photopic and the mesopic objective refraction:

$$P_{sub,sk} = P_{sub} + P_{Dif}. \quad (37)$$

Subsequently, as described above in items 2 and 3, the combination of the refraction $P_{K,sk}$ for mesopic vision is calculated from the subjective refraction for mesopic vision $P_{sub,sk}$ and the objective refraction $P_{obj,sk}$.

This method can be repeated for at least one further (third) pupil diameter, and at least one further combination $P_{K,sk,2}$ may be calculated thus.

From the 3 (at least 2) present refractions $P_K$, $P_{K,sk}$ and $P_{K,sk,2}$ for different pupil diameters, the ideal refraction may be determined by suitable interpolation (e.g. linear) in dependence on the pupil diameter and/or the illumination intensity.

7. Embodiment

A pair of eyes is shown in the following embodiment, wherein subjective refraction data for the left and right eyes were available as well as objective refraction data for the left and right eyes for three different pupil diameters. The exemplary values are listed in table 1, wherein the objective data were obtained in an aberrometer measurement. In table 1, the resulting refraction values for the different described methods are listed as well. The "standard values" result (in accordance with steps 2 and 3) from a combination of the subjective refraction data and the objective refraction data for one pupil diameter.

$$DP_r^1 = DP_l^1 = 3 \text{ mm}, \quad (38)$$

wherein for combination, the equation $$P_K = G_{obj} P_{obj} + G_{sub} P_{sub} \quad (39)$$

with the exemplary weightings $$g_{sub,1} = 0.7 \; g_{sub,2} = 0.6 \; g_{sub,3} = 0.8 \quad (40)$$

is used. The refraction data designated with "light" and "dark" for twilight result from a combination of the objective refraction data on the pupil diameters $$DP_r^2 = DP_l^2 = 5 \text{ mm} \quad (41)$$

and $$DP_r^3 = DP_l^3 = 5.55 \text{ mm} \quad (42)$$

with the subjective data, as has been described above in section 6.

The refraction data designated with "convergence insufficiency", "convergence excess", "exophoria", and "esophoria" result as described above in section 5.

TABLE 1

|  | right | | | left | | | |
|---|---|---|---|---|---|---|---|
|  | Sph [D] | Cyl [D] | A [°] | Sph [D] | Cyl [D] | A [°] | Add [D] |
| Subjective | −5.25 | −1.00 | 3 | −4.25 | −1.75 | 165 | "2.00" |
| Objective pupil diameter 3 mm | −5.02 | −1.58 | 6 | −5.47 | −3.07 | 170 | |
| Objective pupil diameter 5 mm | −4.92 | −1.60 | 3 | −5.12 | −3.75 | 178 | |
| Objective pupil diameter 5.55 mm | −4.88 | −1.61 | 2 | −4.89 | −3.90 | 1 | |
| Result | | | | | | | |
| Standard | −5.40 | −1.22 | 3 | −4.31 | −2.25 | 168 | 2.21 |
| Twilight | | | | | | | |
| Light | −5.30 | −1.26 | 1 | −3.97 | −2.93 | 179 | 2.24 |
| Dark | −5.25 | −1.27 | 179 | −3.71 | −3.13 | 7 | 2.15 |
| Special cases | | | | | | | |
| Convergence insufficiency | −5.58 | −1.22 | 3 | −4.53 | −2.25 | 168 | 2.00 |
| Convergence excess | −5.14 | −1.22 | 3 | −4.00 | −2.25 | 168 | 2.00 |
| Exophoria | −6.02 | −1.22 | 3 | −5.06 | −2.25 | 168 | 2.00 |
| Esophoria | −5.14 | −1.22 | 3 | −4.00 | −2.25 | 168 | 2.00 |

The objective data indicated in table 1 result from aberrometer measurements, which also include Zernike coefficients of higher orders (coma, trefoil, spherical aberration, . . . ). In general, the objective refraction data to be selected also depend on these higher-order coefficients. The type of this dependency is determined by the metric. If the RMS (root mean square) of the wavefront aberration is used as the metric, which is to be minimized for optimum vision, same is minimized exactly by adapting the lower-order coefficients (sphere, cylinder, axis). Thus, the higher-order coefficients in table 1 do not necessarily have to be taken into account in the determination.

One example of a metric in which the higher-order coefficients are needed is the maximum MaxPSF of the PSF (point spread function), which has to be maximized for optimum vision. Table 2 lists the Zernike coefficients of higher order for the right eye for two pupil diameters (the above exemplarily defined pupil diameters $DP_r^2=5$ mm and $DP_r^3=5.55$ mm) and for the left eye for one pupil diameter (the above exemplarily defined pupil diameter $DP_l^3=5.55$ mm).

TABLE 2

| Symbol | Name | Right eye, pupil 5.55 mm | Right eye, pupil 5.0 mm | left eye, pupil 5.55 mm |
|---|---|---|---|---|
| $C_{3,1}$ [μm] | Coma | 0.112933 | 0.0597886 | −1.04653 |
| $C_{3,-1}$ [μm] | Coma | −0.375738 | −0.256975 | 0.344224 |
| $C_{3,3}$ [μm] | Trefoil | 0.0140263 | 0.030974 | −0.0234007 |
| $C_{3,-3}$ [μm] | Trefoil | −0.169401 | −0.122997 | −0.0124213 |
| $C_{4,0}$ [μm] | Sph. aberration | −0.00786817 | −0.0130847 | −0.0616062 |
| $C_{4,2}$ [μm] | Sec. astigm | 0.096995 | 0.0671711 | −0.181049 |
| $C_{4,-2}$ [μm] | Sec. astigm | −0.0780137 | −0.0539008 | −0.209747 |
| $C_{4,4}$ [μm] | Quadrafoil | −0.0390678 | −0.0249956 | 0.10042 |
| $C_{4,-4}$ [μm] | Quadrafoil | 0.0750261 | 0.061365 | 0.059569 |

In table 3, the results in correspondence with table 1 are shown, except that now refraction data obtained from maximizing the metric MaxPSF replace the objective refraction data determined from the RMS. In the line named "result", the combined refraction data of the subjective data with the objective data for the pupil diameter $DP_r^3=5.55$ mm have been used. The refraction data designated with "convergence insufficiency", "convergence excess", "exophoria", and "esophoria" result as described above in section 5.

TABLE 3

|  | Right | | | Left | | | |
|---|---|---|---|---|---|---|---|
|  | Sph [D] | Cyl [D] | A [°] | Sph [D] | Cyl [D] | A [°] | Add [D] |
| Subjective | −5.25 | −1.00 | 3 | −4.25 | −1.75 | 165 | "2.00" |
| Objective with metric pupil diameter 5 mm | −4.72 | −1.39 | 0 | | | | |
| Objective with metric pupil diameter 5.55 mm | −4.68 | −1.41 | 3 | −5.09 | −3.90 | 4 | |
| Result | −5.37 | −1.16 | 3 | −4.13 | −2.52 | 7 | 2.23 |
| Special cases | | | | | | | |
| Convergence insufficiency | −5.50 | −1.16 | 3 | −4.31 | −2.52 | 7 | 2.00 |
| Convergence excess | −5.17 | −1.16 | 3 | −3.86 | −2.52 | 7 | 2.00 |
| Exophoria | −5.83 | −1.16 | 3 | −4.75 | −2.52 | 7 | 2.00 |
| Esophoria | −5.17 | −1.16 | 3 | −3.86 | −2.52 | 7 | 2.00 |

The present invention is not limited to the aforementioned, preferred variants or embodiments. Instead, individual features or feature groups of the individual variants or embodiments may be arbitrarily combined with each other, and further embodiments or variants of the invention can be created thereby.

The invention claimed is:

1. A method for at least one of checking and determining user data of a spectacle lens user, comprising using a microprocessor to perform the following:

providing subjective data of a spectacle lens user, wherein the subjective data including at least subjective refraction data;

providing objective refraction data of the spectacle lens user;

comparing at least a subset of the subjective refraction data with at least a subset of the objective refraction data, and determining a comparative result; and changing one or more values of the subjective refraction data so that at least the subset of the subjective refraction data matches the objective refraction data on the basis of the comparative result provided that the comparative result fulfills at least one predetermined comparative condition, and otherwise, at least one of maintaining at least the subset of the subjective refraction data and providing a message containing the comparative result, wherein at least two of the subjective refraction data, the matched subjective refraction data and the objective refraction data are combined to form combined refraction data, and wherein the combined refraction data designated as $P_K$ are calculated by addition of the objective refraction data designated as $P_{obj}$ with the subjective refraction data designated as $P_{sub}$ as follows:

$$P_K = G_{obj} P_{obj} + G_{sub} P_{sub}$$

wherein:

$$G = \begin{pmatrix} g_1 & 0 & 0 \\ 0 & g_2 & 0 \\ 0 & 0 & g_3 \end{pmatrix},$$

$$0 < g_i < 1,$$

$$G_{obj} + G_{sub} = 1$$

and wherein:

$$P = \begin{pmatrix} M \\ J_0 \\ J_{45} \end{pmatrix}$$

with P representing various power vector possibilities, and $$M = sph + \frac{zyl}{2}$$

$$J_0 = -\frac{zyl}{2}\cos 2A,$$

$$J_{45} = -\frac{zyl}{2}\sin 2A$$

with M, $J_0$ and $J_{45}$ representing an eye's objective refraction values.

2. The method according to claim 1, further comprising:
determining target values of at least one spectacle lens on the basis of at least one of the following data:
a subset of the subjective refraction data,
a subset of the matched subjective refraction data, and
a subset of the objective refraction data.

3. The method according to claim 1, wherein modified objective refraction data are generated on the basis of at least a subset of the objective refraction data and, for determining the comparative result, the modified objective refraction data are compared with at least a subset of the subjective refraction data.

4. The method according to claim 3, wherein several sets of the objective refraction data are provided, and the modified objective refraction data are generated on the basis of the several sets of objective refraction data.

5. The method according to claim 3, wherein the modified objective refraction data are determined taking at least one of the following boundary conditions into account: brightness, pupil diameter, contrast, and age.

6. The method according to claim 3, wherein for calculating the modified objective refraction data, at least one of an aberration function, an OTF, an MTF, a PSF and the standard deviation is used.

7. The method according to claim 1, wherein at least a subset of the objective refraction data is determined by eccentric photorefraction.

8. The method according to claim 1, wherein:

$$g_{sub,j} \geq 0.5.$$

9. The method according to claim 1, wherein:

$g_{sub,1} \geq 0.6$  $g_{sub,2} \geq 0.5$  $g_{sub,3} \geq 0.7$ and Abs($g_{sub,2} - g_{sub,3}$) $\leq 0.3$.

10. The method according to claim 1, wherein:

$g_{sub,1} = 0.7$  $g_{sub,2} = 0.6$  $g_{sub,3} = 0.8$ and Abs($g_{sub,2} - g_{sub,3}$) $\leq 0.1$.

11. The method according to claim 1, wherein a spherical equivalent designated as M of the objective refraction data is determined in a binocular manner, wherein:

$$M^*_{r,obj} := M_{r,obj} - \frac{Dif}{2}$$

$$M^*_{l,obj} := M_{l,obj} + \frac{Dif}{2},$$

wherein $M_{Dif} = M_r - M_l$

Dif=$M_{Dif,obj} - (g_{obj\_bino} M_{Dif,obj} + g_{sub\_bino} M_{Dif,subj})$ $g_{obj\_bino} = 1 - g_{sub\_bino}$ $0 < g_{sub\_bino} < 1$.

12. The method according to claim 11, wherein:

$g_{sub\_bino} \geq 0.6$.

13. The method according to claim 11, wherein:

$g_{sub\_bino} = 0.9$.

14. A non-transitory computer program product which, when loaded into the memory of a computer and executed by a computer, causes the computer to execute a method according to claim 1.

15. An apparatus for at least one of checking and determining user data of a spectacle lens user, comprising:
a subjective data providing device configured to provide spectacle lens user subjective data which includes at least subjective refraction data;
an objective data providing device configured to provide objective refraction data of the spectacle lens user;
a comparing device configured to compare at least a subset of the subjective refraction data with at least a subset of the objective refraction data, and to determine a comparative result; and
a matching device adapted to change one or more values of the subjective refraction data so that at least the subset of the subjective refraction data matches the objective refraction data based on the comparative result provided that the comparative result fulfills at least a predetermined comparative condition, wherein at least one of the matching device is configured to otherwise maintain at least the subset of the subjective refraction data and
the comparing device is configured to provide a message containing the comparative result, wherein at least two of the subjective refraction data, the matched subjective refraction data and the objective refraction data are combined to form combined refraction data, and wherein the combined refraction data designated as $P_K$ are calculated by addition of the objective refraction data designated as $P_{obj}$ with the subjective refraction data designated as $P_{sub}$ as follows:

$P_K = G_{obj} P_{obj} + G_{sub} P_{sub}$ wherein:

$$G = \begin{pmatrix} g_1 & 0 & 0 \\ 0 & g_2 & 0 \\ 0 & 0 & g_3 \end{pmatrix},$$

$0 < g_i < 1,$ $G_{obj} + G_{sub} = 1$ and wherein:

$$P = \begin{pmatrix} M \\ J_0 \\ J_{45} \end{pmatrix}$$

with P representing various power vector possibilities, and $$M = sph + \frac{zyl}{2}$$

$$J_0 = -\frac{zyl}{2}\cos 2A,$$

$$J_{45} = -\frac{zyl}{2}\sin 2A$$

with $M$, $J_0$ and $J_{45}$ representing an eye's objective refraction values.

* * * * *